United States Patent [19]

Rasshofer et al.

[11] 4,386,218

[45] May 31, 1983

[54] POLYAMINES AND PROCESSES FOR THE PRODUCTION OF SUCH POLYAMINES AND OF POLYURETHANE PLASTICS THEREFROM

[75] Inventors: Werner Rasshofer, Cologne; Dieter Dieterich, Leverkusen; Holger Meyborg, Odenthal, all of Fed. Rep. of Germany

[73] Assignee: Bayer Aktiengesellschaft, Leverkusen, Fed. Rep. of Germany

[21] Appl. No.: 308,326

[22] Filed: Oct. 5, 1981

[30] Foreign Application Priority Data

Oct. 21, 1980 [DE] Fed. Rep. of Germany ....... 3039600

[51] Int. Cl.$^3$ ................... C07C 127/15; C07C 127/24
[52] U.S. Cl. ....................................... 564/38; 564/57; 564/59; 564/61; 564/511; 564/512; 560/159; 528/68
[58] Field of Search ..................... 564/38, 57, 59, 61, 564/511, 512; 560/159

[56] References Cited

U.S. PATENT DOCUMENTS

| | | | |
|---|---|---|---|
| 3,955,774 | 5/1976 | Kalopissis et al. | 564/59 X |
| 4,303,780 | 12/1981 | Bellos | 564/38 X |
| 4,324,739 | 4/1982 | Zondler et al. | 564/57 X |

FOREIGN PATENT DOCUMENTS

| | | | |
|---|---|---|---|
| 1155907 | 7/1960 | Fed. Rep. of Germany . | |
| 45-4048410 | 1/1970 | Japan | 564/38 |
| 920475 | 3/1963 | United Kingdom . | |

OTHER PUBLICATIONS

Sidgwick, *Sidgwick's Organic Chem. of Nitrogen*, 3rd edition, pp. 236-237 (1966).
"Spectrophotometric Determination of Aliphatic Isocyanates in the Occupational Atmosphere", *Analyst*, Walker et al., Oct., 1979, vol. 104, pp. 928-936.

*Primary Examiner*—Thomas A. Waltz
*Attorney, Agent, or Firm*—Gene Harsh; Joseph C. Gil; Lyndanne M. Whalen

[57] ABSTRACT

A compound having a terminal isocyanate group is hydrolyzed to produce a polyamine having a urethane and/or a urea and/or a biuret group. More particularly, a carbamate is made by mixing an isocyanate prepolymer having urethane and/or urea and/or biuret groups present with aqueous base solutions at a temperature of from 0° to 0° C. and in quantities such that the equivalent ratio of hydroxyl to isocyanate groups is between from 0.3:1 to ≧1.01 to 1. The carbamate is then treated with an acid ion exchanger to form an amine. The amine is then removed from any other material which may be present. A preferred polyamine thus-produced corresponds to the general formula:

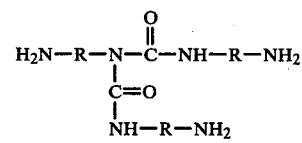

in which each R radical may represent a divalent straight or branched-chain aliphatic radical; a divalent cycloaliphatic radical; a 4,4'- and/or a 2,4'-dicyclohexylmethane radical; or a 2,4- and/or 2,6-methyl cyclohexane radical. Such an amine may be reacted with a polyisocyanate and optionally with other known additives to form a polyurethane plastic or foam.

15 Claims, No Drawings

POLYAMINES AND PROCESSES FOR THE PRODUCTION OF SUCH POLYAMINES AND OF POLYURETHANE PLASTICS THEREFROM

BACKGROUND OF THE INVENTION

This invention relates to polyamines which contain urethane and/or urea groups and/or biuret groups and a process for the production of such polyamines.

It is known that aromatic isocyanates may be converted into primary amines by acid hydrolysis. However, this conversion reaction takes place only to a limited extent, because the amine formed during hydrolysis reacts with the unreacted isocyanate to form the corresponding urea. This secondary reaction cannot be suppressed even when excess strong mineral acid is used. (See e.g., Japanese Pat. No. 55007-827).

German Offenlegungsschrift No. 1,270,046 describes a process for the production of certain primary aromatic amines containing polyalkylene glycol ether segments. In this disclosed process, the reaction products of aromatic di- or tri-isocyanates with polyalkylene glycol ethers and/or polyalkylene glycol thioethers, (preferably those having molecular weights of from 400 to 4000,) are reacted with secondary or tertiary carbinols. The resultant mixture is then subjected to thermal dissociation in an inert solvent (optionally in the presence of acid catalysts). One disadvantage of this process is that, during the course of the thermal dissociation of the urethanes, combustible, volatile alkenes are produced. These alkenes are explosive when mixed with air, so suitable precautionary measures must be taken.

German Auslegeschrift No. 1,694,152 discloses production of prepolymers having at least two terminal amino groups by reacting hydrazine, aminophenylethylamine or other diamines with an NCO-prepolymer. Suitable NCO-prepolymers are made from a polyether polyol and a polyisocyanate (NCO: NH ratio=from 1:1.5 to 1:5). Unreacted amine must be carefully removed in the described process because the amine catalyzes the reaction with polyisocyanate (thereby causing short processing times) and also serves as a reactant.

French Patent No. 1,415,317 describes another possible synthesis for polyamines having urethane groups. In this process, NCO-prepolymers containing urethane groups are converted into the N-formyl derivatives by formic acid, and are subsequently saponified to give terminal aromatic amines. The reaction of NCO-prepolymers with sulphamic acid according to German Auslegeschrift No. 1,155,907 also yields compounds having terminal amino groups. Relatively high molecular weight compounds having aliphatic, secondary and primary amino groups may be obtained according to German Auslegeschrift No. 1,215,373 by reacting relatively high molecular weight hydroxyl compounds with ammonia in the presence of catalysts under pressure at elevated temperatures. U.S. Pat. No. 3,044,989 also discloses a method for making polyamines in which relatively high molecular weight polyhydroxyl compounds are reacted with acrylonitrile and subsequently subjected to catalytic hydration. According to German Offenlegungsschrift No. 2,546,536 or U.S. Pat. No. 3,865,791, relatively high molecular weight compounds having terminal amino groups and urethane groups may be obtained by first reacting NCO-prepolymers with enamines, aldimines or ketimines having hydroxyl groups and then hydrolyzing the reaction product.

SUMMARY OF THE INVENTION

It is an object of the present invention to provide a process for the production of polyamines having urethane and/or urea and/or biuret groups.

It is another object of the present invention to provide polyamines in which urethane and/or urea and/or biuret groups are present.

It is also an object of the present invention to provide a process for the production of polyurethane plastics and foams from polyamines having urethane and/or urea and/or biuret groups.

It is yet another object of the present invention to provide a process in which higher molecular weight polyamines having a substantially improved molecular uniformity may be made without formation of mineral acid salts.

It is a further object of the present invention to provide a process for the production of polyamines having urethane and/or urea and/or biuret groups in which the reaction conditions are mild enough to yield a colorless to slightly yellow product which product is substantially free of impurities.

These and other objects which will be apparent to those skilled in the art are accomplished by hydrolyzing a compound having a terminal isocyanate group to produce a polyamine having urethane and/or urea and/or biuret groups. More particularly, an isocyanate prepolymer having urethane and/or urea and/or biuret groups is mixed with an aqueous base solution preferably aqueous solutions of alkali hydroxides, at a temperature of from 0° to 80° C., preferably of from 0° to 40° C., and in quantities such that the equivalent ratio of hydroxyl to isocyanate groups is from 0.3:1 to greater than 1.01 to 1, preferably 0.3:1 to 1.3:1, and mostly preferred of from 1.01 to 1.3:1. This reaction product is subsequently treated with an acid ion exchanger which exchanger is used in at least an equivalent quantity to form an amine. The amine is subsequently removed from the reaction mixture. The resultant polyamine may be reacted with a polyisocyanate and other known compounds and additives to form a polyurethane plastic or foam.

DETAILED DESCRIPTION OF THE INVENTION

The present invention relates to a process for making an aromatic or aliphatic primary amine containing urethane and/or urea and/or biuret groups which amine may be directly obtained when a slight excess of the corresponding NCO-prepolymer is mixed with aqueous or aqueous/alcoholic bases, such as alkali liquor, and the resulting (alkali) carbamate is treated with an acid ion exchanger. In this process, an NCO-prepolymer having urethane and/or urea and/or biuret groups (optionally dissolved in a water-miscible inert organic solvent,) is introduced into an aqueous alkali hydroxide solution maintained at a temperature of from about 0° to 80° C., (preferably from 0° to 40° C., mostly preferred from 10° to 20° C.) such that the equivalent ratio of hydroxide to NCO-groups in the bases is between 0.3:1 to greater than 1.01:1 (preferably from 0.3:1 to 1.30:1 and especially between 1.01:1 to 1.3:1). The carbamate thus produced is directly converted into the free amine by treating the carbamate with a corresponding acid ion exchanger, which exchanger is used in at least an equivalent quantity. $CO_2$ evolves during such treatment. The free amine may then be separated from the reaction mixture by any of the appropriate techniques known to those in the art.

The present invention also relates to compounds corresponding to the general formula:

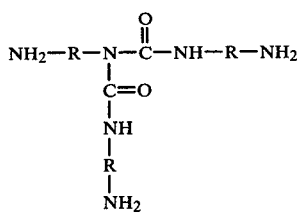

wherein each group may individually represent divalent, straight or branched-chain aliphatic radicals, (preferably tetra-, hexa-, octa-, deca-, undeca- and dodecamethylene radicals, most preferably hexamethylene radicals); divalent cycloaliphatic radicals, such as the 1,3-and/or 1,4-cyclohexane radical, the 4,4'-and/or 2,4'-dicyclohexylmethane radical or the mono-, di-, tri- and tetra- $C_1$-$C_4$ alkyl substituted derivatives thereof, the 2,4- and/or 2,6-methyl-cyclohexane radical and the isophorone radical:

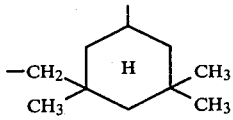

preferably the 4,4'- and/or 2,4'-dicyclohexyl-methane radical, the 2,4- and/or 2,6-methyl-cyclohexane radical and most preferably the isophorone radical). The compounds corresponding to this general formula may be produced from the corresponding known biuret triisocyanates. Such biuret triisocyanates usually contain small fractions (about <10%, by weight) of higher functional biuret polyisocyanates which contain two or more biuret groups. Accordingly, the polyamines produced therefrom also contain higher functional amines having two or more biuret groups.

The present invention is also directed to a process for the production of polyurethane plastics and foams from the polyamines of the present invention. Such polyurethanes may be made by reacting polyisocyanates with the polyamines of the present invention and optionally other low molecular weight and/or high molecular weight compounds having isocyanate-reactive groups, optionally in the presence of known auxiliaries and additives.

The NCO-prepolymer used in the process of the present invention may be produced by techniques well known to those in the art by reacting water and/or compounds containing hydroxyl and/or amino and/or thiol groups (molecular weight from 60 to about 12,000) with an excess of polyisocyanate. In principle, any aliphatic, cycloaliphatic, araliphatic, aromatic or heterocyclic polyisocyanates which are free of hydrolyzable groups, (aside from the NCO-groups) may be used in making such a prepolymer. Suitable materials are described by W. Siefken in Justus Liebigs Annalen der Chemie, 562, pages 75 to 136. Among the isocyanates suitable to the practice of the present invention are those corresponding to the general formula:

Q (NCO)$_n$ wherein
n represents from 2 to 4 (preferably 2); and
Q represents an aliphatic hydrocarbon radical having from 2 to 18 (preferably from 6 to 10) carbon atoms; a cycloaliphatic hydrocarbon radical having from 4 to 15 (preferably from 5 to 10) carbon atoms; an aromatic hydrocarbon radical having from 6 to 15 (preferably from 6 to 13) carbon atoms; or an araliphatic hydrocarbon radical having from 8 to 15, (preferably from 8 to 13) carbon atoms. Examples of such isocyanates include: 1,4-tetramethylene diisocyanate, 1,6-hexamethylene diisocyanate and 1,12-dodecane diisocyanate; cycloaliphatic diisocyanates, in any mixture or the stereo-isomers thereof such as cyclobutane-1,3-diisocyanate, cyclohexane-1,3- and -1,4-diisocyanate, 1-isocyanato-3,3,5-trimethyl-5-isocyanatomethyl-cyclohexane, 2,4- and 2,6-hexahydrotoluylene diisocyanate, hexahydro-1,3- and-/or 1,4-phenylene diisocyanate, perhydro-2,4'-and/or 4,4'-diphenylmethane diisocyanate; aromatic diisocyanates such as 1,3- and 1,4-phenylene diisocyanate, 2,4- and 2,6-toluylene diisocyanate, and mixtures of these isomers, diphenylmethane-2,4'- and/or -4,4'-diisocyanate, including the alkyl and chlorine-substituted derivatives thereof and naphthylene-1,5-diisocyanate. The aromatic diisocyanates are particularly suitable.

Additional examples of isocyanates which may be used in the practice of the present invention are: triphenyl methane-4,4'-4''-triisocyanate; polyphenyl-polymethylene-polyisocyanates obtained by aniline/-formaldehyde condensation followed by phosgenation (described, for example, in British Pat. Nos. 874,430 and 848,671); m- and p- isocyanato-phenyl-sulphonylisocyanates (according to U.S. Pat. No. 3,454,606); perchlorinated aryl polyisocyanates, as described, for example, in German Auslegeschrift No. 1,157,601 (U.S. Pat. No. 3,277,138); norbornane-diisocyanates (according to U.S. Pat. No. 3,492,330); polyisocyanates having isocyanurate groups (described, for example, in U.S. Pat. No. 3,001,973 and in German Pat. Nos. 1,022,789; 1,222,067; 1,027,394; 1,929,034 and 2,004,048); polyisocyanates having urethane groups (described in Belgian Pat. No. 752,261 or U.S. Pat. No. 3,394,164 and 3,644,457); polyisocyanates having acylated urea groups (German Pat. No. 1,230,778) and polyisocyanates produced by telomerization reactions (for example, U.S. Pat. No. 3,654,196).

It is also possible to use the isocyanate group-containing distillation residues from commercial isocyanate production, optionally dissolved in one or more of the above-mentioned polyisocyanates. Mixtures of the above-mentioned polyisocyanates may also be used.

The following materials are preferred isocyanates: the commercially easily accessible polyisocyanates, e.g., 2,4- and 2,6-toluylene diisocyanate and mixtures of these isomers ("TDI"); polyphenyl-polymethylene-polyisocyanates, produced by aniline/formaldehyde condensation and subsequent phosgenation ("crude MDI"); and polyisocyanates having urethane, isocyanurate or urea groups ("modified polyisocyanates"), especially such modified polyisocyanates which are derived from 2,4- and/or 2,6-toluylene diisocyanates or from 4,4'-and/or 2,4'-diphenylmethane diisocyanate.

In the production of the NCO-prepolymers useful in the practice of the present invention, active hydrogen containing compounds having a molecular weight of from 400 to 12,000, particularly from 400 to 5,000, are preferably used. These active hydrogen containing compounds should have at least 2, preferably from 2 to 4, and most preferably 2 or 3 hydroxyl, amino and/or thiol groups (preferably hydroxyl groups). These compounds should also be free from easily hydrolyzable groups, such as ester groups. The polyacetals, polythioethers and in particular, polyethers, conventional in polyurethane chemistry are among the suitable active hydrogen compounds.

The polyethers having at least 2, (usually from 2 to 8) preferably 2 or 3, hydroxyl groups which may be used in the practice of the present invention are known to those in the art. Such polyethers may be, for example, by the auto-polymerization of epoxides, such as ethylene oxide, propylene oxide, butylene oxide, tetrahydrofuran, styrene oxide or epichlorohydrin. This autopolymerization may be carried out in the presence of Lewis catalysts, such as $BF_3$, or by successively adding the epoxides (preferably ethylene oxide and propylene oxide) or a mixture of epoxides to starting components having reactive hydrogen atoms. Such reactive hydrogen-containing reactants include: water, ammonia; alcohols such as ethylene glycol, (1-3) or (1-2)-propylene glycol, trimethylolpropane, glycerin, sorbitol, 4,4'-dihydroxy-diphenyl propane, and amines such as aniline, ethanolamine and ethylene diamine. Sucrose polyethers, as described, for example, in German Auslegeschrift Nos. 1,176,358 and 1,064,938, and polyethers started on formitol or formose (German Offenlegungsschrift Nos. 2,639,083 or 2,737,951) may also be used in the practice of the present invention. Polyethers which have predominantly (i.e. as much as 90 wt. % based on all OH- groups present in the polyether) primary OH- groups are generally preferred. Polybutadienes having OH- groups are also suitable to the practice of the present invention.

The autocondensation products of thiodiglycol or the condensation products thereof with other glycols are thioethers which are particularly suitable to the practice of the present invention.

Polyhydroxyl compounds which contain urethane or urea groups and optionally modified natural polyols may also be used in the practice of the present invention. Addition products of alkylene oxides to phenol/formaldehyde resins or to urea/formaldehyde resins may also be used.

The above-mentioned polyhydroxyl compounds may be modified before use in a number of ways. For example, according to German Offenlegungsschrift Nos. 2,210,839 (U.S. Pat. Nos. 3,849,515) and 2,544,195, a mixture of different polyhydroxyl compounds may be condensed into a higher molecular weight polyol by etherification in the presence of a strong acid to produce a polyol which is composed of different segments linked via ether bridges. German Offenlegungsschrift No. 2,559,372 teaches that it is possible to introduce amide groups into the polyhydroxyl compounds.

Further examples of the compounds which may be used in the practice of the present invention are described in High Polymers, Vol. XVI, "Polyurethanes, Chemistry and Technology" by Saunders-Frisch, Interscience Publishers, New York, London, Vol. I, 1962, pages 32 to 42 and pages 44 to 54 and Vol. II, 1964, pages 5 and 6 and 198 and 199; and in Kunststoffhandbuch Vol. VII, Vieweg-Hochtlen, Carl-Hanser-Verlag, Munich, 1966, on pages 45 to 71. Mixtures of the above-mentioned compounds having at least two isocyanate-reactive hydrogen atoms and a molecular weight of from 400 to 12,000 (e.g. mixtures of different polyethers) may also be used in the practice of the present invention.

In the production of NCO-prepolymers to be used in the present invention, compounds having at least two isocyanate-reactive hydrogen atoms and having a molecular weight of from 18 to 400 (preferably from 60 to 400) may also be included as starting components. These compounds include water and/or compounds having hydroxyl groups and/or amino groups and/or thiol groups, (preferably hydroxyl groups) known in polyurethane chemistry as chain-extenders or cross-linking agents. These low molecular weight compounds usually have from 2 to 8, preferably from 2 to 4, isocyanate-reactive hydrogen atoms. Mixtures of different compounds having at least two isocyanate-reactive hydrogen atoms and a molecular weight of from 18 to 400 may also be used.

Examples of such low molecular weight reactive hydrogen compounds are: water, ethylene glycol, (1,2)- and (1,3)- propylene glycol, (1,4)- and (2,3)- butylene glycol and (1,5)-pentane diol, (1,6-)-hexane diol, (1,8)-octane diol, neopentyl glycol, 1,4-bis-hydroxymethyl-cyclohexane, 2-methyl-1,3-propane diol, dibromobutene diol (U.S. Pat. No. 3,723,392), glycerine trimethylolpropane, (1,2,6)- hexane triol, trimethylolethane, pentaerythritol, quinitol, mannitol, sorbitol, castor oil, di- and tri- and tetra- ethylene glycol, di-, tri-, and tetra-propylene glycol, dibutylene glycol and higher polyethylene-, polypropylene- or polybutylene-glycols having a molecular weight up to 400, 4,4'-dihydroxy-diphenylpropane, dihydroxymethylhydroquinone, ethanolamine, diethanolamine, N-methyldiethanolamine, triethanolamine and 3-aminopropanol.

Mixtures of hydroxyaldehydes and hydroxy-ketones ("formose") or polyhydric alcohols ("formitol") produced by reduction of formose are also included among the suitable low molecular weight polyols. Formose may be produced by the autocondensation of formaldehyde hydrate in the presence of a metal compound catalyst and a co-catalyst which is a compound capable of enediol formation (See e.g., German Offenlegungsschrift Nos. 2,639,084; 2,714,084; 2,714,104; 2,271,186; 2,738,154 and 2,738,512).

Aliphatic diamines which are suitable to the practice of the present invention include: ethylene diamine, 1,4-tetramethylene diamine, 1,6-hexamethylene diamine, 1,12-dodecamethylene diamine and mixtures thereof, 1-amino-3,3,5-trimethyl-5-amino-methyl cyclohexane ("isophorone diamine"), 2,4- and 2,6-hexahydro toluylene diamine and mixtures thereof, perhydro-2,4'- and 4,4'-diamino diphenylmethane, p-xylylene diamine, bis-(3-aminopropyl)-methylamine, diamino-perhydroanthrazenes (German Offenlegungsschrift No. 2,638,731) and cycloaliphatic triamines according to German Offenlegungsschrift No. 2,614,244. Hydrazine and substituted hydrazines such as methylhydrazine, are also suitable.

Appropriate aromatic diamines are: diamines having ether groups (according to German Offenlegungsschrift Nos. 1,770,525 and 1,809,172 (U.S. Pat. No. 3,654,364 and 3,736,295); 2-halogen-1,3-phenylene diamines optionally substituted in the 5-position (German Offenlegungsschrift Nos. 2,001,772; 2,025,896 and 2,065,869); 3,3'-dichloro-4,4'-diaminodiphenylmethane; toluylene diamine; 4,4'-diaminodiphenylmethane; 4,4'-diaminodiphenyl disulfides (German Offenlegungsschrift No. 2,404,976); diaminodiphenyl dithioether (German Offenlegungsschrift No. 2,509,404); aromatic diamines substituted by alkylthio groups (German Offenlegungsschrift No. 2,638,760); aromatic diamines containing sulfonate or carboxylate groups (German Offenlegungsschrift No. 2,720,166); and the high-melting diamines mentioned in German Offenlegungsschrift No. 2,635,400. Examples of appropriate aliphatic-aromatic diamines are the amino-alkyl-thioanilines according to German Offenlegungsschrift No. 2,734,574.

The prepolymers having free isocyanate groups may be produced by reaction in the melt or in solution in accordance with procedures known to those in the art. The equivalent ratio of NCO groups to active hydrogen atoms (preferably OH groups) should be greater than 1, and is generally from 1.5:1 to 2.8:1. It is, of course, possible to use a greater excess of polyisocyanate. The prepolymers generally have an oily to waxy consistency depending on the starting materials. If the NCO/OH ratio is higher than 2:1, then prepolymers which are not substantially extended are obtained. If the NCO/OH ratio is lower than 2:1, the average molecular weight of the prepolymer is increased. It is also possible to use a proportionate amount of low molecular weight polyols as chain-lengthening agents in the production of the prepolymers in addition to higher molecular weight starting materials. Where such low molecular weight polyols are used, higher molecular weight prepolymers are also obtained.

Preferred prepolymers for the process of the present invention are obtained from relatively high molecular weight polyether glycols (optionally while also using chain-lengtheners of the type described above) and aliphatic and/or aromatic diisocyanates in an equivalent ratio of from 1:1.5 to 1:2.8, (preferably about 1:2). Ureas containing NCO groups produced by reaction of NCO compounds with water or aromatic or aliphatic amines are also preferred. Biurets containing NCO groups produced by reaction of NCO compounds (preferably aliphatic diisocyanates) with an excess of water or by reaction of ureas with NCO compounds are particularly preferred. The NCO-content of the prepolymers lies between 0.5 and 37.5%, preferably 0.7 and 27% by weight.

All substances which have acidic hydrogen atoms moveable in an insoluble polymeric matrix are suitable acid ion exchangers which may be used in the practice of the present invention. Ion exchange resins which have a styrene/divinyl benzene skeleton as the polymeric matrix, to which are attached sulfonic acid groups as acid functions are particularly suitable.

In the process of the present invention, the prepolymer is usually dissolved in a water-miscible, inert solvent. Suitable solvents are, for example, dimethoxy ethane (DME), tetrahydrofuran and dioxan. In such a solution, from 1 to 400 parts of the prepolymer may be used for each 100 parts of solvent.

In making the polyamines of the present invention, the prepolymer should be slowly mixed (preferably dropped into the aqueous base solution over a period of from 30 to 120 minutes), with stirring, with a solution of alkali metal or alkaline earth metal hydroxide or other strong bases, such as tetra alkyl ammonium hydroxides or sodiumaluminates, in water and/or alcohol. The alkali metal or alkaline earth metal hydroxide solution should be at a temperature of from 0° to 40° C. before the addition of the prepolymer. This temperature range should be preferably maintained during the mixing with the prepolymer. The concentration of the base, e.g. alkali metal or alkaline earth metal in the solution should preferably be 1 part by weight of base for each 5 to 20 parts, by weight, of water or alcohol. Organic and inorganic ammonium hydroxides (e.g. tetraalkyl ammonium hydroxide) are also suitable.

If the process of the present invention is carried out without a solvent, the NCO-prepolymer should have as low a viscosity as possible (preferably up to about 5000 Mpas). The NCO-prepolymer should be added to the alkali metal or alkaline earth metal hydroxide solution in as finely dispersed form as possible (e.g. introduced by injecting through a nozzle) at a high stirring speed and the quantity of water present in the basis solution may be increased (e.g. by a factor from 1.1 to 100) to facilitate stirring. The isocyanate-containing prepolymer may also be heated to a temperature of from 30° to 90° C. before it is added to the basic solution. The NCO-prepolymer or its solution may also be metered into a reaction chamber (such as a static mixer or stirring chamber mixing device) together with the base and may stay in a vessel until the reaction is completed. The quantity of the base, e.g. alkali metal or alkaline earth metal hydroxide, should be present in a quantity such that when the reaction with the NCO-prepolymer has been completed, at least a small quantity of free base remains. An NCO/OH ratio of from 1:1.01 to 1:1.30 and use of alkali metal hydroxides are preferred in this reaction. The concentration of residual base should not be too high, however, because after the formation of the carbamate is complete the urethane groups present in the prepolymer will be hydrolyzed. In order to improve the homogeneity of the solutions, a commercially available emulsifier may be used. Such an emulsifier is generally used in quantities of from 0.1 to 1 parts, by weight, preferably about 0.5 parts by weight, (based on 100 parts of reaction mixture). When mixing the NCO component with the hydroxide component, it is advisable to stir the mix intensively in order to avoid local concentration differences. After the addition of prepolymer has been completed, the mixture should preferably be stirred for another 15 to 180 minutes at from 0° to 20° C. It is, however, also possible to use an NCO/hydroxyl-ion-relation with less base, e.g. a relation from 1:0.3 to 1:1, whereby then the fraction of the polycarbamates or polyamines, which are "pre-extended" by urea groups and have a higher molecular weight and higher viscosity, will increase.

In the second step of the process of the present invention, the carbamate solution or suspension is mixed with the ion exchanger. It makes no difference whether the acid ion exchange resin is added to the carbamate suspension or solution (Process A) or whether the reverse procedure is adopted (Process B). The ion exchange resin and carbamate component should be mixed in a proportion such that the intensity of the evolution of gas can be withstood by the apparatus for a period of from 10 to 300 minutes.

The evolution of gas begins after about ¼ of the total quantity of ion exchange resin has been added. When the components are mixed, a temperature increase occurs. It is advantageous to maintain the temperature from 10° to 70° C. External heating, if necessary, may be used. Ion exchanger is added until gas evolution ceases. Heating the mixture to from 60° to 100° C. for a short period of time expels any dissolved carbon dioxide.

The reverse process i.e., introducing the ion exchanger into the carbamate, is particularly preferred when the reaction data are known and also in the case of a continuous process.

The reaction mixture is basic at the end of the reaction. The basicity of this mixture corresponds to the free amine content and the base strength of the product amine. The product-containing reaction mixture may then be further treated to separate out the product amine. If the amine is soluble in the reaction mixture, it is separated from the ion exchange resin by filtration and the aminic solution is freed from solvent by distillation. If the amine is slightly soluble in the reaction mixture, a suitable solvent is added until the amine dissolves; the amine is then recovered in the same manner as described for a soluble amine. If the amine is insoluble in the reaction mixture, it is filtered off from the liquid medium. The residue is then treated with a suitable solvent until the amine dissolves. The resultant amino solution is then treated in the same manner as a soluble amine. The product polyamines are freed from traces of volatile components by heating them to a temperature from 60° to 80° C. at from 0.01 to 0.1 Torr.

The solvents which are suitable for such separation procedures are aprotically-dipolar water-miscible solvents, such as N-methylpyrrolidone, dimethylformamide and dimethylsulfoxide etc.

The ion exchange resins neutralized by the reaction may be regenerated according to known methods and may be easily reused.

Due to the low vapor pressure of the polyamines produced by the process of the present invention, the polyamines are preferably used as reactants in the production of polyurethane plastics. When used in this manner, the product polyamines may also be mixed with other low molecular weight (molecular weight: from 32 to 399) and/or relatively high molecular weight (molecular weight: from 400 to about 15,000) compounds having isocyanate-reactive groups. Suitable starting materials for the production of polyurethane plastics were mentioned above in connection with preparation of the prepolymer used in the process of the present invention. Appropriate materials for production of polyurethanes are also described in German Offenlegungsschrift Nos. 2,302,564; 2,432,764 (U.S. Pat. No. 3,963,679); 2,639,083; 2,512,385; 2,513,815; 2,550,796; 2,550,797; 2,550,833; 2,550,860 and 2,550,862. These publications also described auxiliary agents and additives which may optionally be used in polyurethane production. Polyurethane ureas may also be produced from the polyamines of the present invention by procedures known to those in the art.

Other applications for the polyamines produced according to the present invention include, for example, coupling components for diazo dyes, hardeners for epoxide and phenyl resins, and all other known reactions of amines, such as amide or imide formation etc.,.

Compared to conventional processes, the present process has the following surprising advantages:

(1) In the production of the NCO-prepolymers from polyisocyanates and compounds containing NCO-reactive hydrogen atoms, small portions of monomeric isocyanate often remain in the prepolymer. These monomeric isocyanates are also converted to amino compounds in the first step of the present invention. It has been found however, these low molecular weight polyamines form complexes with the ion exchanger in the present process while the higher molecular weight polyamines do not. The low molecular weight polyamines may therefore be removed from the reaction mixture by treating the mixture with an ion exchanger. Consequently, higher molecular weight polyamines with a considerably improved molecular-uniformity are obtained by the present invention without formation of a mineral acid salt intermediate.

(2) The ion exchanger may be added to the carbamate solution or suspension or the carbamate solution may be added to the ion exchanger. Either process yields equally good results.

(3) The process conditions according to the present invention are very mild. Consequently, the product polyamines (including aromatic polyamines) which are generally colorless to slightly yellow contain virtually no impurities and at a substantially slower rate than less pure polyamines.

(4) The process conditions of the present invention are mild so sensitive polyamines containing biuret groups may be produced readily. Such compounds represent a new class of biuret polyamines.

(5) In the process of the present invention more than the equivalent quantity of acid ion exchanger (based on the H-atoms) may be used without converting the higher molecular weight polyamines into the corresponding salts, which would require an additional processing step to remove the undesirable salt by-product.

Having thus described our invention, the following Examples are given by way of illustration. Quantities given in these Examples are to be understood as parts by weight, or percent by weight, unless otherwise indicated.

EXAMPLES

Example 1

1a. Production of the carbamate 200 g of a compound (containing 1.12 mols of NCO, NCO value=23) obtained by the biuretization of 1,6-diisocyanato-hexane were dissolved in 200 ml of dioxane. This solution was added dropwise over a period of 30 minutes to a solution of 67.2 g (1.2 mols) of KOH and 0.1 g of the emulsifier sold under the trademark Mersolat H in 200 ml of water. The temperature of the reaction mixture was maintained at 10° to 15° C. throughout this addition by means of external cooling. The mixture was stirred for an additional 30 minutes at 10°–15° C.

1b. Production of the amine (Process A)

680 g of moist ion exchanger sold under the trademark Lewatit SC 108 were added in portions over a period of 150 minutes to the mixture of 1a. The temperature was maintained at 60° to 70° C. During this process, 20 l of $CO_2$ evolved. When the gas evolution was substantially completed, the mixture was mixed with 1 liter of dioxane and heated to 90° C. for 10 minutes. During this heating procedure, 5.1 liters of $CO_2$ evolved. The total gas yield of 25.1 liter was 98.8% of the theoretical amount. The hot mixture was then suction filtered from solid ion exchanger. 80 g (46.8%) of a resinous product which was only slightly yellow in color and which had the correct $^1$H-NMR-spectrum was obtained by destilling the solvent out of the filtrate. This product corresponded to the formula

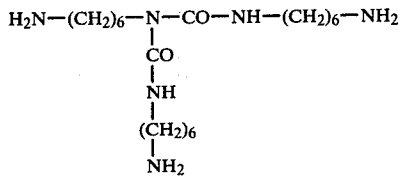

Lewatit SC 108 (Bayer) is a strongly acid cation exchanger having $SO_3H$— groups in a gel-like divinyl benzene/styrene matrix (8% cross-linked having a particle size of from 0.3 to 1.5 mm). The total capacity is 2 milliequivalents/1 ml of moist resin or 4.5 milliequivalents/1 g of dry resin. The useful cpacity of the moist resin is approximately 1.3 milliequivalents/ml and that of the dry resin is 3 m. equivalents/g.

This process was repeated using a number of different commercially available ion exchange resins (described below). In each case, the polyamine was obtained in a yield and purity comparable to that recovered in 1b. The resins used in these procedures were:

1c. The resin sold under the trademark Lewatit S 100 (Bayer) is a strongly acid cation exchanger having —$SO_3H$— groups in a styrene/divinyl benzene matrix. The total capacity is 2.2 milliequivalents/ml of moist resin, the useful capacity up to 1.8 milliequivalents/ml (apparent weight from 800 to 900 g/l moist resin).

1d. Lewatit SP 112 (Bayer) which is a strongly acid cation exchanger having $SO_3$—H groups and average cross-linking in a macroporous, fine-pore styrene/divinyl benzene matrix. The total capacity is approximately 1.9 milliequivalents/ml of moist resin, the useful capacity is up to 1.3 milliequivalents/ml (apparent weight from 700 to 800 g/l of moist resin).

1e. The resin sold under the trademark Lewatit SP 120 (Bayer) which is a strongly acid cation exchanger having $SO_3H$— groups and high cross-linking density in a macroporous, large-pore styrene/divinyl benzene matrix. The total capacity is 1.9 milliequivalents/ml of moist resin, the useful capacity is up to 30 g of CaO/l of moist resin (apparent weight from 700 to 800 g/l of moist resin).

1f. The resin sold under the tradename Lewasorb A 10 (Bayer) which is an exchanger of the Lewatit 100-type (H-form) ground to a particle size of <0.2 mm.

Further information concerning the ion exchanger resins used may be found in the following publications by Bayer AG: OC/I 1379; OC/I 1350; OC/I 20026; OC/I 20031; OC/I 20303 and OC/I 20333.

All of the ion exchangers which were used in these Examples were converted into the $H^{\oplus}$-form and were washed until they were free of acid with distilled water prior to use.

1g. Comparative Example

The carbamate prepared in 1a. was treated with mineral acid and the resulting salt was neutralized with KOH. A solid product was obtained with only about 30 to 50% $CO_2$-gas yield. The product was largely insoluble due to urea formation.

EXAMPLE 2

Process A

2a. Production of the NCO-prepolymer 1 kg of a polypropylene diol started on propylene glycol, having an OH number of 56, an average molecular weight of 2000 and <5% primary OH groups was dehydrated by heating at 80° C. for 5 hours under 15 Torr. This polyol was added dropwise to 174 g (1 mol) of 2,6-diisocyanato toluene over 5 hours at 80° C. The mixture was stirred at 80° C. for another 90 minutes. The NCO-prepolymer thus-produced had an NCO value of 3.3% (theoretical=3.58). Prepolymers were obtained in the same manner using the same starting components, which prepolymers had an NCO value of 4.92% (corresponds to 2.79% of free 2,6-diisocyanato toluene) and 3.4% respectively.

2b. Production of the carbamate 9.6 g (172 mol) of potassium hydroxide and 0.1 g of Mersolat H were dissolved in 50 ml of water. A solution of 200 g of the prepolymer described above (3.3% NCO) in 200 ml of dry dioxane was added dropwise to the potassium hydroxide solution over a period of one hour. During this addition, temperature of the reaction mixture was maintained at 10° C. After the addition was completed, the mixture was stirred for an additional 15 minutes to complete the reaction.

2c. Production of the amine 84 g of the ion exchange resin sold under the name Lewasorb A 10 were added to the carbamate suspension of 2b. over a period of one hour using a powder metering funnel. The temperature was maintained in the range from 20° to 40° C. 3.05 liter of $CO_2$ (86.6% of the theoretical amount) evolved. The ion exchange resin was removed from the reaction mixture by suction filtration and washed with 350 ml of dioxane. The dioxane washings were combined and the dioxane was distilled off. 178 g of a faintly yellow liquid (91.5% yield) were recovered exhibiting the following data:

| | |
|---|---|
| prim. base-nitrogen | 0.82 |
| Molecular weight$^{(+)}$ | 2580 (theoretical 2296) |
| NH value: | 41 (20° C.) |
| | 59 (60° C.) |
| | 53 (100° C.) |

$^{(+)}$vapor pressure osmometric measurement of molecular weight

The theoretical NH value of an amine with a molecular weight of 2580 is 43.4.

2d. A carbamate was produced from 5246 g of the prepolymer prepared in 2a. (dissolved in 4 liter of dry dioxane) having an NCO value of 3.4, 280 g of KOH and 3 g of Mersolat H in a total of 1 liter of water. This carbamate was then mixed with 4012 g of Lewatit SP 120 (H-form, water moist), (4 hours at room temperature, 2 hours at 50° C.) and treated in the same manner as described in 2c. The amine thus-produced was characterized as follows:

| | |
|---|---|
| Yield: | 4400 g of faintly colored oil (85.7% of the theoretical yield) |
| Molecular weight | 2420 (theoretical 2296) |
| NH-value: | 39.4 |

The theoretical NH value of an amine with a molecular weight of 2420 is 46.

PROCESS B

2e. The prepolymer and carbamate were produced in the same manner as described in 2a. and 2b. 150 g of the ion exchange resin sold under the trademark Lewatit 5100 and 100 ml of water were combined. 200 g of the carbamate were added dropwise at room temperature over a period of 20 minutes. The mixture was stirred for an additional 2 hours while being maintained at a temperature of from 40° to 45° C. The CO₂ gas which evolved amounted to 3.1 liter (88.6% of the theoretical amount). The ion exchange resin was then separated from the reaction mixture and the solvent was distilled off.

140 g (72% of the theoretical yield) of a practically colorless viscous liquid remained. This product had the following characteristics: Molecular weight 2380,2330 (theoretical 2296) When titrated with 0.1 N HClO₄, 7.62 ml of 0.1 N HClO₄ were required to neutralize each gram of the product amine. This titration data corresponds to 2.0 mols of $NH_2$ with an molecular weight of 2620. (1.81 mols of $NH_2$ with an molecular weight of 2380 would be the corresponding value to the molecular weight(+)). 1.75 mols of $NH_2$ with an molecular weight of 2296 would be the theoretical value corresponding to the composition according to the used components.
(+)vapor pressure osmometric measurements

EXAMPLE 3

3a. An NCO-prepolymer was prepared from approximately 3 mols of diisocyanato toluene and 1 mol of trimethylol propane by the procedure described in Example 2a. The NCO value of the triisocyanate thus-produced was 16.2 (theoretical NCO value 18.8).

3b. 44.8 g (0.8 mol) of KOH and 0.2 g of the material sold under the trademark Mersolat H were dissolved in 150 ml of water. This solution was then mixed with a solution of 200 g of the triisocyanate prepared in 3a. in 200 ml of dry dioxane at from 5° to 10° C. over a period of 30 minutes. The reactant mixture was stirred for an additional 30 minutes while being maintained at a temperature of from 5° to 10° C.

3c. A mixture of 654 g of the ion exchange resin sold under the trademark Lewatit SP 120 (H-form, water moist) and 393 g of the ion exchange resin sold under the trademark Lewatit SP 112 were added in small portions to the carbamate suspension prepared in 3b. This addition was completed after 195 minutes. The reaction temperature was maintained at from 60° to 65° C. 13.9 liter of CO₂ (80.3% of the theoretical amount) evolved. The solid substance was separated from the liquid by filtration and the amine was washed from the ion exchanger using 1.8 liter of hot dioxane. After repeated filtration, the dioxane was distilled off. 146 g (81% of the theoretical yield) of a yellowish product were obtained. This product which had a melting range of from 95° to 115° C. was characterized as follows:

| Molecular weight | 960 (theoretical = 702) |
|---|---|
| NH-value (20° C.): | 159–160 (theoretical = 175) |

EXAMPLE 4-PRODUCTION OF AN INTEGRAL FOAM

Formulation A:

| 100 g | of the amine obtained according to Example (2c) |
|---|---|
| 14 g | of butane-1,4-diol |
| 1 g | of ethylene glycol |
| 8 g | of trichloromonofluoromethane |
| 0.02 g | dibutyltin dilaurate |
| 0.3 g | triethylene diamine |
| 77 g | of a liquid diphenylmethane-4,4'-diisocyanate, modified by a reaction with excess quantities of dipropylene glycol, having an NCO content of 22 wt. %. |

Formulation B:

| 100 g | of the amine obtained according to Example (2c) |
|---|---|
| 30 g | of ethylene glycol |
| 8 g | of trichlorofluoromethane |
| 0.02 g | of dibutyltin dilaurate |
| 0.2 g | of triethylene diamine |
| 190 g | of a liquid diphenylmethane-4,4'-diisocyanate modified by a reaction with excess quantities of dipropylene glycol, having an NCO content of 22 wt %. |

All of the components in each of the above-described formulations with the exception of the isocyanate were intensively mixed for 30 seconds at 25° C. using a high speed stirrer. The isocyanate component was then added, the mixture was intensively mixed for an additional 10 seconds using a high-speed stirrer and foamed into a free foam mold.

The following data were obtained:

$T_1$ = starting time (time in seconds after the isocyanate component has been stirred in, at which the mixture commences to foam);
$T_2$ = rise time (time in seconds after the isocyanate component has been stirred in, after which the rise procedure is completed);
$T_3$ = non-tacky (time in seconds after the isocyanate component has been stirred in, after which the surface of the foam is no longer tacky);
$T_4$ = plucking time (time in seconds after the isocyanate component has been stirred in, after which it is no longer possible to pull small pieces out of the foam by hand.)

| | $T_1$ | $T_2$ | $T_3$ | $T_4$ |
|---|---|---|---|---|
| Formulation A | 12 | 33 | 33 | 40 |
| Formulation B | 22 | 36 | 36 | 36 |

The plastic material produced from Formulation A exhibited slight shrinkage and was slightly elastic. The plastic material produced from Formulation B was substantially harder than that of Formulation A and did not exhibit any shrinkage.

EXAMPLE 5-PRODUCTION OF A FLEXIBLE FOAM 100 g of the amine obtained according to Example 2c., 3 g of water, 0.5 g of a foam stabilizer based on a polysiloxane-polyalkylene oxide block copolymer, 0.1 g of diethylaminoethanol, 0.2 g of N-methyl-N'-dimethylamino-piperazine and 0.05 g of tin-II-di-(2-ethylhexanoate) were combined at 25° C. and intensively mixed for 30 seconds using a high-speed mixer. 36.0 g of toluylene diisocyanate (80% 2,4- and 20% 2,6-isomers) were then added and the mixture was stirred intensively for 5 seconds using a high-speed mixer and poured out immediately.

$T_1$ = 6 seconds (Starting time)
$T_2$ = 62 seconds (Rise time)

The product foam was cured for 10 minutes at 90° C. It had a closed-cell appearance and a high elasticity.

EXAMPLE 6

Preparation of the Carbamate

Into 27.2 g of an ice-cooled 50% KOH-solution (0.243 mol KOH), 490 g water and 0.5 g Mersolat ® H are added 500 g of a 60° C. warm NCO-prepolymer (OH$^\ominus$: NCO=0.6:1). The NCO-prepolymer was prepared from toluylene diisocyanate and a polypropylene glycol ether of an average molecular weight 2000 and has an NCO-content of 3.4%. The temperature of the reaction is kept between 20°–24° C. by cooling. One liter of methanol is added and mixture is stirred further 45 minutes.

PREPARATION OF THE AMINE

To the above mentioned reaction mixture is then added 290 ml of Lewatit SC-108. The evolution of slowly split off carbondioxide is increased by warming up to 55° C.

After the carbondioxide evolution has ceased, the reaction mixture is filtered and the loaded ion exchange resin is washed with 1.5 liters of methanol and is again filtered. Both filtrates are put together and the solvents are distilled at 20 mbar/100° C. and then 0.15 mbar/80° C. Yield: 400 g (82%).

| Product data: | |
| --- | --- |
| NH-number: | 10,4 (mg KOH/g) |
| Acid number: | 0,1 (mg KOH/g) |
| Molecular weight | 10 500 |
| Viscosity ($\eta^{75°C}$) | 61000 mPa.s |
| Water content (K. Fischer method) | 0,14% |

What is claimed is:

1. A process for the production of a polyamine having urethane and/or urea and/or biuret groups by hydrolysis of a compound having terminal isocyanate groups comprising:
   (a) mixing an isocyanate prepolymer having urethane and/or urea and/or biuret groups with an aqueous base solution at a temperature of from 0° to 80° C. and in a quantity such that the equivalent ratio of hydroxyl to isocyanate groups is between from 0.3:1 to $\geq$1.01:1,
   (b) treating the product of (a) with an acid ion exchanger to form an amine, and
   (c) separating the product amine from any other materials present.

2. The process of claim 1 wherein the acid ion exchanger is added to the product of (a) in at least a stoichiometric quantity.

3. The process of claim 1 wherein the isocyanate prepolymer is a reaction product of (i) a polyether having two or three hydroxyl groups and a molecular weight of from 400 to 5,000, (ii) a polyisocyanate and optionally, (iii) a polyol having a molecular weight of from 62 to 400 which reaction product is made by using quantities of reactants such that the NCO/OH ratio is from 1.5:1 to 2.8:1.

4. The process of claim 1 wherein the isocyanate prepolymer is a reaction product of (i) an OH compound having a molecular weight of from 18 to 400 and (ii) a polyisocyanate made by reacting (i) and (ii) in quantities such that the NCO/OH ratio is from 1.5:1 to 2.8:1.

5. The process of claim 1 wherein the NCO prepolymer is a biuretized aliphatic diisocyanate.

6. The process of claim 1 wherein the isocyanate prepolymer is a solution in a water-miscible inert organic solvent.

7. The process of claim 1 wherein the temperature at which the isocyanate prepolymer is mixed with the solution of the bases is from 0° to 40° C.

8. The process of claim 1 wherein the equivalent ratio of hydroxyl ion to isocyanate groups is from 0.3:1 to 1.30:1.

9. The process of claim 1 wherein the equivalent ratio of hydroxyl ion to isocyanate groups is from 1.01:1 to 1.30:1.

10. The process of claim 1 in which from 0.1 to 1 parts by wt., based on 100 parts reaction mixture, of an emulsifier are added in step (a).

11. The process of claim 1 in which the base is an alkali metal hydroxide in the form of a 5–20 wt. % solution.

12. A polyamine corresponding to the general formula:

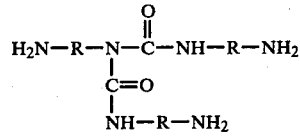

in which each R radical may independently represent a divalent straight- or branched- chain, aliphatic radical, a divalent cycloaliphatic radical, a 4,4'- and/or a 2,4'-dicyclohexylmethane radical or a 2,4- and/or 2,6-methyl cyclohexane radical.

13. The polyamine of claim 9 wherein at least one R radical represents a hexamethylene radical.

14. The polyamine of claim 9 wherein at least one R radical represents an isophorone radical.

15. A polyamine corresponding to the general formula:

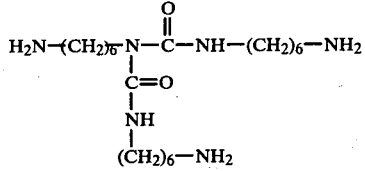

* * * * *